(12) United States Patent
Rampoldi et al.

(10) Patent No.: US 7,303,755 B2
(45) Date of Patent: Dec. 4, 2007

(54) PHARMACEUTICAL COMPOSITIONS WITH ANTIBIOTIC ACTIVITY

(75) Inventors: Luca Rampoldi, Lainate (IT); Luca Pirrone, Legnaro (IT); Sarah Faccin, Mestre (IT); Alessandro Grassano, Monza (IT); Giovanni Gurrieri, Grezzana (IT)

(73) Assignee: Zambon S.p.A., Bresso (IT)

( * ) Notice: Subject to any disclaimer, the term of this patent is extended or adjusted under 35 U.S.C. 154(b) by 420 days.

(21) Appl. No.: 10/615,781

(22) Filed: Jul. 10, 2003

(65) Prior Publication Data

US 2004/0022866 A1 Feb. 5, 2004

(30) Foreign Application Priority Data

Aug. 1, 2002 (IT) .......................... MI2002A1725

(51) Int. Cl.
*A61K 9/00* (2006.01)
*A61K 9/14* (2006.01)
*A61K 33/00* (2006.01)
*A01N 59/00* (2006.01)

(52) U.S. Cl. ...................... 424/400; 424/489; 424/601; 424/602; 424/606; 424/715; 424/717; 514/2

(58) Field of Classification Search ................ 424/400, 424/489, 601, 602, 606, 715, 717; 514/2
See application file for complete search history.

(56) References Cited

U.S. PATENT DOCUMENTS

| | | | |
|---|---|---|---|
| 3,852,434 A | 12/1974 | Kahan et al. | |
| 4,716,153 A | 12/1987 | Morishita et al. | |
| 4,727,065 A | 2/1988 | Chiarino et al. | |
| 4,783,449 A | 11/1988 | Meola | |
| 4,863,908 A | 9/1989 | Chiarino et al. | |
| 5,162,309 A | 11/1992 | Tentorio et al. | |
| 5,191,094 A | 3/1993 | Tentorio et al. | |
| 2003/0078215 A1* | 4/2003 | Shastri et al. ................. | 514/34 |
| 2004/0077626 A1* | 4/2004 | Hester et al. ........... | 514/211.15 |

FOREIGN PATENT DOCUMENTS

| | | |
|---|---|---|
| DE | 197 12 565 | 10/1998 |
| EP | 0 027 597 | 4/1981 |
| EP | 0 498 243 | 8/1992 |
| FR | 2 690 340 | 10/1993 |
| GB | 2 013 682 | 8/1979 |
| GB | 2 025 975 | 1/1980 |
| PT | 94816 | 4/1991 |
| WO | WO 94/20072 | 9/1994 |
| WO | WO 03/045435 A1 | 6/2003 |

OTHER PUBLICATIONS http://web.archive.org/web/20020217115418/http://www.rxlist.com/cgi/generic2/fosfomycin.htm (2002).*
A. L. Barry, et al., Antimicrobial Agents and Chemotherapy, vol. 35, No. 6, pp. 1235-1238, "In Vitro Susceptibility Testing Procedures for Fosfomycin Tromethamine", Jun. 1991.

* cited by examiner

*Primary Examiner*—Johann R. Richter
*Assistant Examiner*—Konata M. George
(74) *Attorney, Agent, or Firm*—Oblon, Spivak, McClelland, Maier & Neustadt, P.C.

(57) ABSTRACT

The use of certain salts and aminoacids as stabilizer of the antibiotic Fosfomycin Tromethamol and pharmaceutical compositions containing them, is described.

15 Claims, No Drawings

PHARMACEUTICAL COMPOSITIONS WITH ANTIBIOTIC ACTIVITY

The present invention concerns the use of certain salts and aminoacids as stabilizer of the antibiotic Fosfomycin Tromethamol and pharmaceutical compositions containing them. Fosfomycin Tromethamol (hereinafter FT) (The Merck Index XIII Ed., No. 4277, page 755), is a known antibiotic used for the treatment of urinary tract infections and it is the active ingredient, for example, of the drug named MONURIL®.

FT is a compound relatively unstable because it presents reactive functional groups and can easily degrade due to the temperature and the humidity.

This make difficult the storage of the raw material, the working and the preparation of pharmaceutical compositions (today exclusively in the form of hydrosoluble granulate) and the storage of the ready packages.

For its use the granulate is dissolved in water and drunk. The acidity of the stomach too, may cause significant degradation phenomena which, in practice, reduce the amount of the active ingredient available to the absorption.

We have now surprisingly found that some substances, when used in mixture with FT, are able to stabilize the antibiotic making it easier to handle for the operations of pharmaceutical technology and making stable the ready packages for a longer time.

Furthermore, the degradation of FT at the pH of gastric juice results to be decreased when FT is in association with those substances.

Therefore, the object of the present invention is the use of a substance selected from:
tribasic sodium or potassium citrate
monoacidic sodium or potassium citrate
tribasic sodium or potassium phosphate
monoacidic sodium or potassium phosphate
sodium or potassium carbonate
sodium or potassium bicarbonate
sodium or potassium tartrate
arginine
lysine or mixtures thereof, to stabilize Fosfomycin Tromethamol.

A second object of the present invention are the pharmaceutical compositions containing Fosfomycin Tromethamol, a compound selected from:
tribasic sodium or potassium citrate
monoacidic sodium or potassium citrate
tribasic sodium or potassium phosphate
monoacidic sodium or potassium phosphate
sodium or potassium carbonate
sodium or potassium bicarbonate
sodium or potassium tartrate
arginine
lysine or mixtures thereof, and excipients suitable for the pharmaceutical use.

Hereinafter, the substances the use of which is object of the invention will be jointly indicated as "stabilizer", meaning with that term also mixtures of two or more substances.

The amount of stabilizer to be used is between 10% and 100% in moles with respect of FT, preferably between 30% and 70% and still more preferably about 50%.

Among the above reported stabilizers, the presently preferred are tribasic sodium citrate, sodium or potassium carbonate or bicarbonate and arginine.

The pharmaceutical compositions object of the invention are prepared from FT and the stabilizer by adding excipients for pharmaceutical use.

The pharmaceutical form of FT presently preferred is that of hydrosoluble granules since, due to the relatively high amount of FT to be administered according to the instant posology (5.631 g), the solution obtained from the dissolution of granules in water is the most suitable and well accepted by the patients.

With the new compositions of the invention it is possible to obtain formulations in granules but it is also possible to prepare hydrosoluble compositions obtainable by a simple admixture of FT, stabilizer and the other excipients, if any.

Suitable excipients for the preparation of hydrosoluble compositions containing FT and a stabilizer are for example natural as well as artificial sweeteners or flavouring.

Even if it is possible to add further excipients, useful for example for the granulation process, their use seems not to be necessary.

The preparation of compositions of the invention can be conveniently carried out in different ways.

It is possible, for example, to prepare a semimanufactured granulate of FT to which successively the stabilizer, the flavouring and the sweetening are mixed and finally the whole is distributed in sachets.

Alternatively, all the ingredients of the formulation can be mixed directly together.

With the aim to better illustrate the present invention, the following examples are now given.

EXAMPLE 1

The stabilization of FT from the selected stabilizers was evaluated experimentally with the DSC technology.

A mechanic mixture of FT (0.02 moles) with each of the stabilizers (0.01 moles) was admixed with 0.05% of water with respect to FT.

The DCS technology used for each mixture (scanning 10° C./min.) allow to measure the reaction heat which develops after the melting peak of FT, due to the degradation reaction.

A reduced heat development indicates a higher stabilization, the amount of FT being the same.

The following values were obtained:

| | |
|---|---|
| FT (single substance) = | 271.03 ± 16.73 (J/g) |
| FT + sodium citrate tribasic (dihydrate) = | 119.19 ± 7.47 (J/g) |
| FT + sodium bicarbonate = | 143.32 ± 4.92 (J/g) |
| FT + sodium carbonate = | 115.84 ± 9.89 (J/g) |
| FT + arginine = | 175.25 ± 9.41 (J/g) |

The obtained data show as FT was effectively stabilized by adding the above mentioned substances. The heat of the degradation reaction, with the same amount of FT, was reduced in percentages between about 35 and 70%.

EXAMPLE 2

The stabilization of FT in simulated gastric juice was evaluated by reproducing the use conditions of the patient: 5.631 g of FT were additioned with 0.01 moles of the selected stabilizer and were dissolved in water (180 ml).

The solution was poured in simulated gastric juice (100 ml, pH 1) and the degradation was measured as percentage recovery of the active ingredient in time.

Already after 30 minutes the recovery of FT without stabilizer was 82% while with the stabilizer the recovery was 90%.

EXAMPLE 3

The following pharmaceutical compositions were prepared by simple admixture of the ingredients.

| Composition 1 | |
| --- | --- |
| Fosfomycin Tromethamol | 5.631 g |
| Sodium citrate dihydrate | 1.125 g |
| Aspartame | 0.100 g |
| Tangerine flavour | 0.100 g |
| Orange flavour | 0.100 g |

| Composition 2 | |
| --- | --- |
| Fosfomycin Tromethamol | 5.631 g |
| Sodium citrate dihydrate | 0.500 g |
| Sodium bicarbonate | 0.840 g |
| Aspartame | 0.100 g |
| Tangerine flavour | 0.100 g |
| Orange flavour | 0.100 g |

| Composition 3 | |
| --- | --- |
| Fosfomycin Tromethamol | 5.631 g |
| Sodium bicarbonate | 1.127 g |
| Sodium carbonate | 0.200 g |
| Sucrose | 2.000 g |
| Tangerine flavour | 0.100 g |
| Lemon flavour | 0.100 g |

| Composition 4 | |
| --- | --- |
| Fosfomycin Tromethamol | 5.631 g |
| Sodium citrate dihydrate | 0.734 g |
| Sodium citrate monoacid | 0.987 g |
| Fructose | 2.500 g |
| Tangerine flavour | 0.100 g |
| Lemon flavour | 0.100 g |

| Composition 5 | |
| --- | --- |
| Fosfomycin Tromethamol | 5.631 g |
| L-arginine | 1.470 g |
| Sodium Saccharin | 0.010 g |
| Sucrose | 2.100 g |
| Tangerine flavour | 0.100 g |
| Orange flavour | 0.100 g |

| Composition 6 | |
| --- | --- |
| Fosfomycin Tromethamol | 5.631 g |
| L-arginine | 0.500 g |
| Lysine | 0.100 g |
| Aspartame | 0.100 g |
| Tangerine flavour | 0.100 g |
| Orange flavour | 0.070 g |

| Composition 7 | |
| --- | --- |
| Fosfomycin Tromethamol | 5.631 g |
| Sodium citrate dihydrate | 0.500 g |
| Sodium carbonate | 0.500 g |
| Aspartame | 0.100 g |
| Tangerine flavour | 0.070 g |
| Orange flavour | 0.070 g |

| Composition 8 | |
| --- | --- |
| Fosfomycin Tromethamol | 5.631 g |
| Sodium citrate dihydrate | 1.000 g |
| L-arginine | 0.050 g |
| Aspartame | 0.070 g |
| Orange flavour | 0.150 g |
| Lemon flavour | 0.030 g |

| Composition 9 | |
| --- | --- |
| Fosfomycin Tromethamol | 5.631 g |
| Sodium citrate dihydrate | 1.800 g |
| Sodium saccharin | 0.040 g |
| Sucrose | 1.500 g |
| Tangerin flavour | 0.100 g |
| Lemon flavour | 0.100 g |

| Composition 10 | |
| --- | --- |
| Fosfomycin Tromethamol | 5.631 g |
| Sodium citrate dihydrate | 1.125 g |
| Sorbitol | 1.000 g |
| Aspartame | 0.070 g |
| Tangerine flavour | 0.100 g |
| Orange flavour | 0.100 g |

What is claimed is:

1. A process for stabilizing a Fosfomycin Tromethamol composition, the process comprising:
    combining Fosfomycin Tromethamol with at least one of the following substances in an amount effective to stabilize the Fosfomycin Tromethamol:
    a tribasic sodium citrate;
    a tribasic potassium citrate;
    a monoacidic sodium citrate;
    a monoacidic potassium citrate;
    a tribasic sodium phosphate;
    a tribasic potassium phosphate;
    a monoacidic sodium phosphate;
    a monoacidic potassium phosphate;

a sodium carbonate;
a potassium carbonate;
a sodium bicarbonate;
a potassium bicarbonate;
a sodium tartrate;
a potassium tartrate;
an arginine; and
a lysine.

2. The process of claim 1, wherein the stabilizing substance is one or more of: a tribasic sodium citrate, a sodium carbonate, a potassium carbonate, a sodium bicarbonate, a potassium bicarbonate, and an arginine.

3. The process of claim 1, wherein a molar ratio of the substance with respect to Fosfomycin Tromethamol is in a range between 10% and 100%.

4. The process of claim 1, wherein a molar ratio of the substance with respect to Fosfomycin Tromethamol is in a range between 30% and 70%.

5. The process of claim 1, wherein a molar ratio of the substance with respect to Fosfomycin Tromethamol is at least 50%.

6. The process of claim 1, wherein the Fosfomycin Tromethamol and the stabilizing agent are produced as a hydrosoluble granulate.

7. The process of claim 1, wherein the Fosfomycin Tromethamol is present in the composition in an amount of approximately 5.6 g.

8. The process of claim 1, further comprising adding an excipient agent.

9. A pharmaceutical composition comprising Fosfomycin Tromethamol and at least one substance, in an amount effective for stabilizing, selected from the group consisting of:
a tribasic sodium citrate;
a tribasic potassium citrate;
a monoacidic sodium citrate;
a monoacidic potassium citrate;
a tribasic sodium phosphate;
a tribasic potassium phosphate;
a monoacidic sodium phosphate;
a monoacidic potassium phosphate;
a sodium carbonate;
a potassium carbonate;
a sodium bicarbonate;
a potassium bicarbonate;
a sodium tartrate;
a potassium tartrate;
an arginine; and
a lysine.

10. The pharmaceutical composition of claim 9, wherein the stabilizing substance is one or more of: a tribasic sodium citrate, a sodium carbonate, a potassium carbonate, a sodium bicarbonate, a potassium bicarbonate, and an arginine.

11. The pharmaceutical composition of claim 9, wherein a molar ratio of the substance with respect to Fosfomycin Tromethamol is in a range between 10% and 100%.

12. The pharmaceutical composition of claim 1, wherein a molar ratio of the substance with respect to Fosfomycin Tromethamol is in a range between 30% and 70%.

13. The pharmaceutical composition of claim 1, wherein a molar ratio of the substance with respect to Fosfomycin Tromethamol is at least 50%.

14. The pharmaceutical composition of claim 1, wherein the Fosfomycin Tromethamol is present in an amount of approximately 5.6 g.

15. The pharmaceutical composition of claim 1, which is produced as a hydrosoluble granulate.

* * * * *